United States Patent
Lauer (10) Patent No.: US 11,564,842 B2
(45) Date of Patent: Jan. 31, 2023

(54) HEMOSTATIC ABSORBENT PRODUCT FOR MUCOSAL MEMBRANES, KIT CONTAINING THE SAME, AND METHOD OF USING THE SAME

(71) Applicant: Daniel Stuart Lauer, Palm Beach Gardens, FL (US)

(72) Inventor: Daniel Stuart Lauer, Palm Beach Gardens, FL (US)

(*) Notice: Subject to any disclaimer, the term of this patent is extended or adjusted under 35 U.S.C. 154(b) by 161 days.

(21) Appl. No.: 15/760,474

(22) PCT Filed: Oct. 3, 2016

(86) PCT No.: PCT/US2016/055165
§ 371 (c)(1),
(2) Date: Mar. 15, 2018

(87) PCT Pub. No.: WO2017/062309
PCT Pub. Date: Apr. 13, 2017

(65) Prior Publication Data
US 2018/0256403 A1    Sep. 13, 2018

Related U.S. Application Data (63) Continuation of application No. 14/875,188, filed on Oct. 5, 2015, now abandoned.

(51) Int. Cl.
*A61F 13/00* (2006.01)
*A61F 17/00* (2006.01)

(52) U.S. Cl.
CPC .. *A61F 13/00042* (2013.01); *A61F 13/00012* (2013.01); *A61F 13/00029* (2013.01);
(Continued)

(58) Field of Classification Search
CPC .......... A61F 13/00012; A61F 13/00029; A61F 13/00042; A61F 13/00068;
(Continued)

(56) References Cited

U.S. PATENT DOCUMENTS 1,561,020 A * 11/1925 Pond .................... A61F 5/0093
604/287
2,877,767 A * 3/1959 Kramer ................ A61M 31/00
604/11
(Continued)

FOREIGN PATENT DOCUMENTS

| RU | 2108077 | 4/1998 |
|---|---|---|
| RU | 2469668 | 12/2012 |

OTHER PUBLICATIONS

Technical Data Sheet, SUNTOUCH(R) Nasal Dressing, Huizhou Foryou Medical Devices Co. Ltd File No. JS-73-091 Ver. 1.2, Revised Date Aug. 11, 2010.

*Primary Examiner* — Adam Baker
(74) *Attorney, Agent, or Firm* — Duane Morris LLP; Gregory M. Lefkowitz (57) ABSTRACT

A kit that includes an absorbent product adapted for mucosal membrane hemostasis, and instructions using the absorbent product is disclosed. The absorbent product can include a liquid permeable pouch, and at least one sheet of absorbent material within the liquid permeable pouch. The instructions can include rolling and/or folding the absorbent product, placing the rolled and/or folded absorbent product proximate the site of the bleeding, and applying pressure to the absorbent product. The instructions can also include inserting the absorbent product into a mucous membrane, such as a nostril or the vaginal canal. Methods of utilizing the absorbent product and the kit are also disclosed.

15 Claims, 9 Drawing Sheets

(52) U.S. Cl.
CPC ........ *A61F 13/00068* (2013.01); *A61F 17/00* (2013.01); *A61F 2013/00106* (2013.01); *A61F 2013/00463* (2013.01)

(58) Field of Classification Search
CPC .......... A61F 13/00072; A61F 13/00059; A61F 13/2005; A61F 13/2008; A61F 13/126; A61F 13/2048; A61F 13/2057; A61F 13/2011; A61F 13/2068; A61F 13/204; A61F 2013/00106; A61F 2013/00463; A61F 2013/00468; A61F 2013/00476; A61F 2013/00714; A61F 2013/00217; A61F 2013/00119; A61F 2013/00153; A61F 2013/4581; A61F 2013/4568; A61F 15/001; A61F 15/004; A61F 13/15; A61F 13/20; A61F 13/36; A61F 13/45; A61F 13/472; A61F 13/475; A61F 13/26; A61F 2013/15382; A61F 2013/15373; A61F 2013/15365; A61F 2013/2031; A61F 2013/2034; A61F 2013/2037; A61F 2013/2024; A61F 6/08; A61F 6/142; A61F 6/144; A61F 6/146; A61F 13/2002; A61F 13/2017; A61F 13/202; A61F 13/2022; A61F 13/2031; A61F 13/2034; A61F 13/2037; A61F 13/2042; A61F 13/20572; A61F 13/2065; A61F 13/2071; A61F 13/38

See application file for complete search history.

(56) References Cited

U.S. PATENT DOCUMENTS

| | | | | |
|---|---|---|---|---|
| 3,570,489 | A * | 3/1971 | Brown | A61F 13/2011 604/374 |
| 3,815,600 | A * | 6/1974 | Groves | A61M 31/002 604/286 |
| 3,986,511 | A * | 10/1976 | Olofsson | A61F 13/2048 604/385.18 |
| 3,999,549 | A * | 12/1976 | Poncy | A61F 13/2051 604/15 |
| 4,041,948 | A * | 8/1977 | Flam | A61F 13/2051 604/375 |
| 6,191,341 | B1 * | 2/2001 | Shippert | A61F 13/2051 602/47 |
| 6,258,075 | B1 * | 7/2001 | Taylor | A61F 13/2051 604/385.18 |
| 6,293,931 | B1 * | 9/2001 | Romare | A61F 13/47218 604/385.101 |
| 6,768,040 | B1 * | 7/2004 | Sessions | A61F 13/126 128/206.11 |
| 8,597,267 | B2 * | 12/2013 | Noel | A61F 13/2051 604/382 |
| 2002/0042378 | A1 | 4/2002 | Reich | |
| 2005/0147656 | A1 * | 7/2005 | McCarthy | A61L 33/08 424/445 |
| 2006/0036228 | A1 * | 2/2006 | Noda | A61F 13/47209 604/385.17 |
| 2006/0247592 | A1 * | 11/2006 | Schmidt-Forst | A61F 13/2085 604/385.18 |
| 2007/0083137 | A1 | 4/2007 | Hopman et al. | |
| 2008/0077105 | A1 * | 3/2008 | Hooi | A61F 13/2071 604/385.18 |
| 2008/0283426 | A1 * | 11/2008 | Primer | G09F 3/0289 206/232 |
| 2010/0130907 | A1 * | 5/2010 | Linkel | A61F 13/2065 604/11 |
| 2010/0262090 | A1 | 10/2010 | Reisinger | |
| 2014/0142523 | A1 * | 5/2014 | Steinbaugh | A61L 15/60 604/304 |

* cited by examiner

HEMOSTATIC ABSORBENT PRODUCT FOR MUCOSAL MEMBRANES, KIT CONTAINING THE SAME, AND METHOD OF USING THE SAME

CROSS-REFERENCE TO RELATED APPLICATIONS

This application is a § 371 national stage entry of International Application No. PCT/US2016/055165, filed on Oct. 3, 2016, which claims priority to U.S. patent application Ser. No. 14/875,188, filed on Oct. 5, 2015, the entire contents of which are incorporated herein by reference.

FIELD OF THE INVENTION

The present invention relates generally to hemostatic absorbent products, particularly, hemostatic absorbent products adapted for use in mucosal membranes.

BACKGROUND

Individuals experience bleeding of the mucous membranes from time-to-time. The cause of these bleeding incidents can range from surgical procedures, to bloody noses, to tooth eruption and exfoliation generally experienced by children, to menstruation, as well as, accidents. While medical professionals and consumers frequently use gauze to treat such situations, gauze does not retain blood and other bodily fluids well. In addition, both professionals and consumers have difficulty visualizing and localizing regular gauze to the area in need of hemostasis.

SUMMARY

In one embodiment, a kit that includes an absorbent product adapted for mucosal membrane hemostasis, and instructions for applying the absorbent product to bleeding tissue is provided. The absorbent product can include a pre-sized liquid permeable pouch, and an absorbent material contained within the liquid permeable pouch.

In another embodiment, a kit that includes an absorbent product adapted for mucosal membrane hemostasis, and instructions using the absorbent product is provided. The absorbent product can include a liquid permeable pouch, and at least one sheet of absorbent material within the liquid permeable pouch. The instructions can include rolling and/or folding the absorbent product, placing the rolled and/or folded absorbent product proximate the site of the bleeding, and applying pressure to the absorbent product.

In another embodiments, a method of hemostasis in a mucosal membrane is provided. The method can include providing an absorbent product that includes a liquid permeable pouch, and at least one sheet of absorbent material contained within the liquid permeable pouch; placing the absorbent product proximate the site of the bleeding; and applying pressure to the absorbent product. In some embodiments, the pressure can be applied using the teeth opposing the site of the bleeding or, in the case of the nasal cavity, digital pressure on the outside skin of the nasal cavity bilaterally.

These and other features, objects and advantages of the present invention will become more apparent to one skilled in the art from the following description and claims when read in light of the accompanying drawings.

BRIEF DESCRIPTION OF THE DRAWINGS

FIG. 11A is an environmental view showing a folded absorbent product that has been placed between two teeth in a space where a tooth has fallen out or been removed, while

FIG. 12A is an environmental view showing a rolled absorbent product placed into a nostril to facilitate hemostasis of a bloody nose (i.e., epistaxis), while

DETAILED DESCRIPTION

Figure 1:
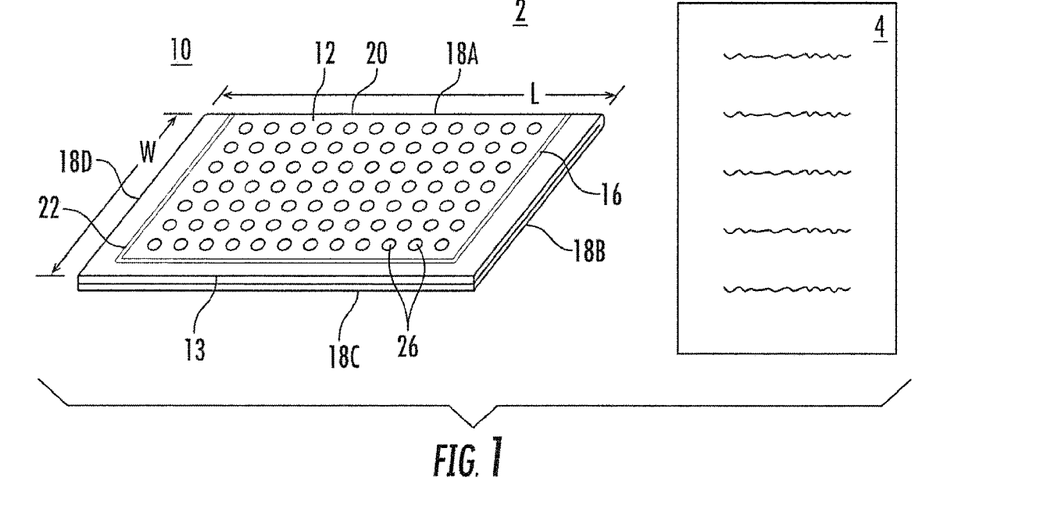
FIG. 1 is a front, perspective view of a kit containing an absorbent product and instructions.
Figure 2:
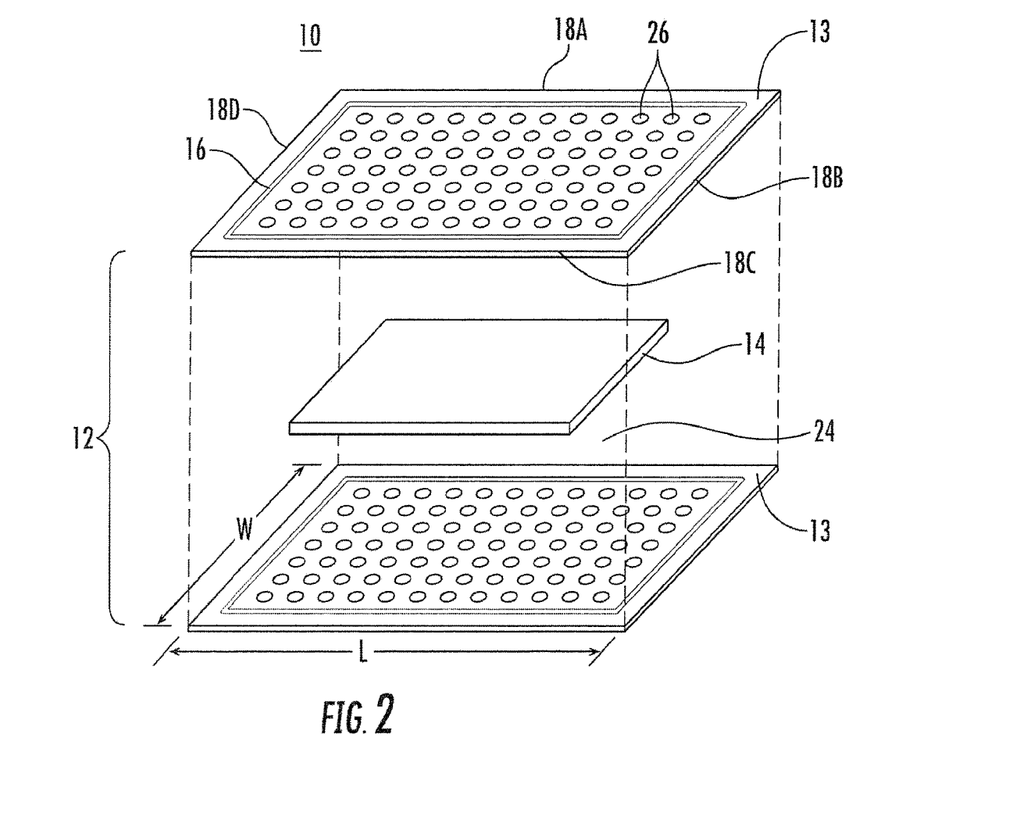
FIG. 2 is an exploded view of an absorbent product with a liquid permeable pouch formed of two sheets of pouch material sealed together to form an enclosed space containing a sheet of absorbent material.

As shown in FIG. 1, a kit 2 containing an absorbent product 10 for facilitating hemostasis in a mucosal membrane, and instructions 4 for applying the absorbent product to bleeding tissue is disclosed. FIGS. 1-18 show a variety of absorbent products 10 and applications of the absorbent products 10 as described herein. The absorbent product 10 can include a liquid permeable pouch 12 and an absorbent material 14 contained within the liquid permeable pouch 12.

In some embodiments, the liquid permeable pouch 12 can be formed of a liquid permeable sheet 13 of material. In some embodiments, the liquid permeable pouch 12 is formed of more than one liquid permeable sheet 13 of material. In some embodiments, the liquid permeable sheet 13 of material comprises a thermoplastic material. In some embodiments, the thermoplastic can be selected from the group including, but not limited to, polyethylene, polypropylene, polystyrene, polyvinyl chloride, fluoropolymers (e.g., polytetrafluoroethylene), polybenzimidazole, nylon, polyacrylate, and combinations thereof. The liquid permeable sheet 13 of material can be inherently permeable or can include apertures 26. Although some figures show the liquid permeable pouch 12 including apertures 26, it should be understood that the apertures may be present in the natural structure of the material, such as holes in a mesh, spunbond, or meltblown material, in some embodiments. Alternately, the apertures 26 can be holes that were punched in a material (e.g., a film) to make it appropriate for use as the liquid permeable pouch 12.

In some embodiments, the liquid permeable pouch 12 can be hydrophilic in order to allow blood to pass into the absorbent product and contact the absorbent material 14. In some embodiments, the liquid permeable pouch 12 can be a mesh, such as a nylon mesh, which facilitates fluid intake into the absorbent. This can enhance the rate of fluid absorbed by the absorbent product 10. In some embodiments, the liquid permeable pouch 12 can be formed from a material that is naturally hydrophobic (e.g., a polymer), but is treated to make an outer surface of the liquid permeable pouch 12 hydrophilic. In some embodiments, an interior surface of the liquid permeable pouch 12 proximate the absorbent material 14 is hydrophobic. In this manner, the liquid permeable pouch 12 can facilitate transfer of blood into the absorbent product 10, while preventing the blood from exiting the liquid permeable pouch 12.

In some embodiments, a surface (e.g., an exterior surface) of the liquid permeable pouch 12 can be treated to make it more hydrophilic or wettable. For example, the exterior surface of the pouch can be treated with a surfactant, a plasma treatment, a corona treatment, a poloxamer or other copolymer treatment solution or other surface treatment (e.g., pluronics available from BASF). For example, Saati-Care Hyphyl™ nylon mesh, which is treated with a surfactant coating exhibiting superb hydrophilic properties.

In some embodiments, the liquid permeable pouch 12 can be formed of a material with an open area ranging from 25-60%, or from 28-50%, or from 30-40%, or any combination of these ranges. In some embodiments, the liquid permeable pouch 12 can be formed of a material with a mesh opening ranging from 50-250 μm, or from 60-200 μm, or from 65-150 μm, or any combination of these ranges. In some embodiments, the liquid permeable pouch 12 can be formed of a material with a basis weight ranging from 20-150 $g/m^2$, or from 25-100 $g/m^2$, or from 27-75 $g/m^2$, or from 30-60 $g/m^2$, or any combination of these ranges. In some embodiments, the liquid permeable pouch 12 can be formed of a material with a mesh count ranging from 50-250 per cm, or from 75 to 230 per cm, or from 100 to 225 per cm, or from 150 to 220 per cm, or any combination of these ranges.

In some embodiments, the pores or apertures 26 in the liquid permeable pouch 12 can be designed to allow blood to pass into the absorbent product 10, while preventing more viscous bodily fluids, such as mucous and clots, from passing into the absorbent product 10. For example, the size of the pores and/or apertures and the surface wettability treatments applied to the liquid permeable pouch 12 can be adjusted to achieve this goal.

In some embodiments, the liquid permeable pouch 12 is thermally bonded to form a seal 16. In other embodiments, the seal 16 of the liquid permeable pouch 12 can be formed using thermal bonding, adhesive bonding, and/or ultrasonic bonding techniques. In some embodiments, each perimeter edge 18A, 18B, 18C, 18D of the liquid permeable pouch is either folded 20, thermally bonded 22 (including, but not limited to, radiofrequency bonding and ultrasonic bonding), or adhesively bonded 22. In some embodiments, as in FIGS. 1 and 16, the liquid permeable pouch 12 can be formed from one liquid permeable sheet 13 using one folded perimeter edge 18A and three perimeter edges that are bonded 18B, 18C, 18D. In some other embodiments, as in FIG. 2, the liquid permeable pouch 12 can be formed from two liquid permeable sheets 13 that are bonded on all three perimeter edges 18A, 18B, 18C, 18D. In some embodiments, as in FIGS. 17-18, the liquid permeable pouch 12 can be formed from a liquid permeable sleeve 13 and have one or more perimeter end edges that are bonded 18A, 18B. As used herein, the "perimeter edge" refers to the edge itself and areas immediately adjacent to the edge. Examples of seals 16 extending along perimeter edges are shown in the figures.

In some embodiments, the entire pouch 12 forms an enclosed space 24 surrounding the absorbent 14 using a single, continuous seal 16, with or without folded edges 20. For example, FIGS. 2-4 & 13 show embodiments where a single, continuous seal is used to form a pouch 12 defining an enclosed space 24. For example, FIGS. 1 & 5 show embodiments where a single, continuous seal and a folded edge 20 are used to form a pouch 12 defining an enclosed space 24. As used herein, "enclosed space" is intended to encompass spaces that are in fluid communication with the external environment through porosity (including apertures) in the sheets 13 used to form the liquid permeable pouch 12, while the bulk absorbent material 14 is retained within the pouch 12.

In some embodiments, the liquid permeable pouch 12 and/or sheets 13 forming the same include or are a nonwoven material, while the liquid permeable pouch 12 and/or sheets 13 can include or can be woven materials (e.g., mesh, gauze, etc.) in other embodiments. Examples of non-woven materials include, but are not limited to, spunbond, meltblown, polymeric film with apertures, bonded-carded webs (BCW), paper, polymer stabilized materials, filter paper, hydroentangled materials, and combinations thereof. In some embodiments, the liquid permeable pouch 12 and/or sheets 13 can be formed of a polymer containing nonwoven, which may be treated with a surfactant. In some embodiments, the liquid permeable pouch 12 and/or sheets 13 can be formed of a cellulosic material including, but not limited to, paper, polymer stabilized paper, filter paper, hydroentangled materials, and combinations thereof, which may be treated with a surfactant.

In some embodiments, the liquid permeable pouch 12 and/or sheets 13 include a plurality of apertures 26. In other embodiments, the liquid permeable pouch 12 and/or sheets 13 are permeable because it is formed from a permeable material, e.g., spunbond, mesh, BCW, polymeric film with apertures, paper, polymer stabilized paper, filter paper, etc.

In some embodiments, wherein the absorbent material 14 comprises a cellulosic material. Cellulosic materials can include both woven and non-woven materials. Examples of woven cellulosic materials include, but are not limited to, gauze and meshes. Examples of non-woven cellulosic materials include, but are not limited to, paper, polymer stabilized paper, filter paper, hydroentangled materials.

In some embodiments, the absorbent material 14 comprises a polymeric absorbent. Examples of polymeric absorbents includes, but are not limited to, polyvinyl alcohol (PVA) absorbents. In some embodiments, the polymeric absorbent is an open celled foam (e.g., a PVA foam). In some embodiments, the polymeric and/or foam absorbent can have a shape selected from a cylinder, a sphere, a rectangular solid, a cube, a trapezoid, a pyramid, a sheet, variations of these shapes, or other shapes.

In some embodiments, as shown in FIGS. 2-6 & 14, there is a gap between the edge of the absorbent material 14 and the seal 16. In some embodiments, the gap is at least 0.1 cm, or at least 0.2 cm, or at least 0.3 cm. This gap enables the absorbent material 14 to swell as it absorbs fluids, such as blood, mucous, or menses. In addition, the swelling helps the absorbent product stay in place once inserted into a nostril, a tooth socket, or a vaginal cavity.

In some embodiments, absorbent material 14 includes a stabilized sheet comprising cellulosic material or foam (e.g., PVA foam). Examples of stabilized sheets containing cellulosic materials include, but are not limited to, paper, polymer stabilized paper, filter paper, and hydroentangled materials. Examples of cellulosic materials include, but are not limited to, wood fibers, modified cellulosic materials (e.g., cellophane and rayon) and combinations thereof. Exampled of modified cellulose materials include, but are not limited to, cellulose acetate, cellulose triacetate, cellulose propionate, cellulose acetate propionate (CAP), cellulose acetate butyrate (CAB), nitrocellulose (cellulose nitrate), cellulose sulfate, and combinations thereof.

In some embodiments, the absorbent material 14 can have a rapidity rate for water of at least 200 ml/min, or at least 300 ml/min, or at least 400 ml/min. In some embodiments, the absorbent material 14 can have a rapidity rate of up to 800 ml/min, or up to 700 ml/min, or up to 600 ml/min, or up to 500 ml/min. In some embodiments, the absorbent material (e.g., filter paper) is designed to remove fine particles larger than 10 µm, or larger than 15 µm, or larger than 20 µm, or larger than 25 µm.

Figure 3:
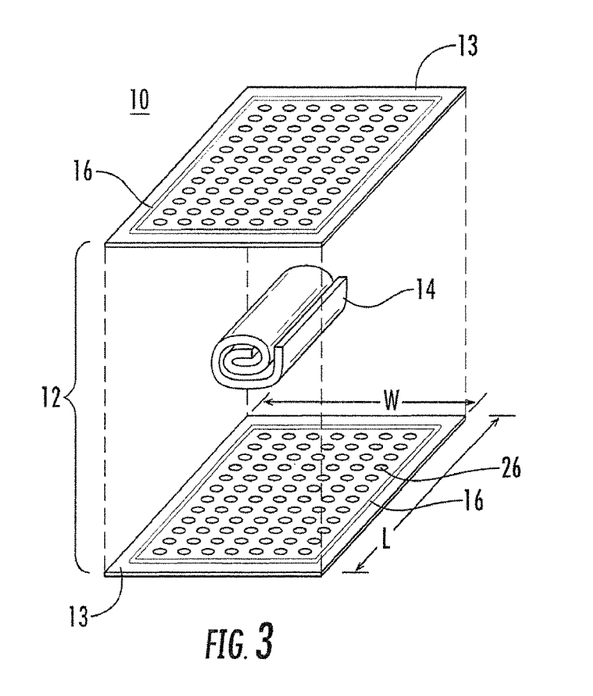
FIG. 3 is an exploded view of an absorbent product with a liquid permeable pouch formed of two sheets of pouch material sealed together to form an enclosed space containing a sheet of rolled absorbent material.
Figure 4:
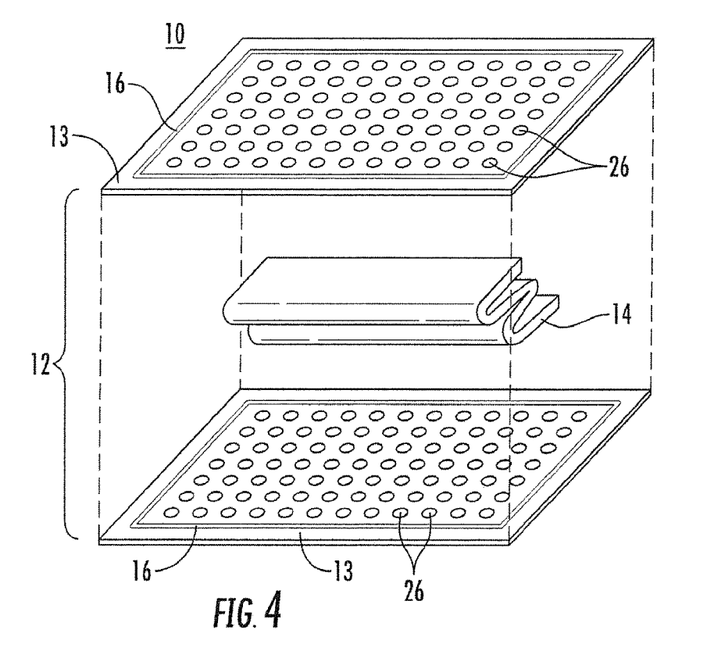
FIG. 4 is an exploded view of an absorbent product with a liquid permeable pouch formed of two sheets of pouch material sealed together to form an enclosed space containing a folded sheet of absorbent material.
Figure 5:
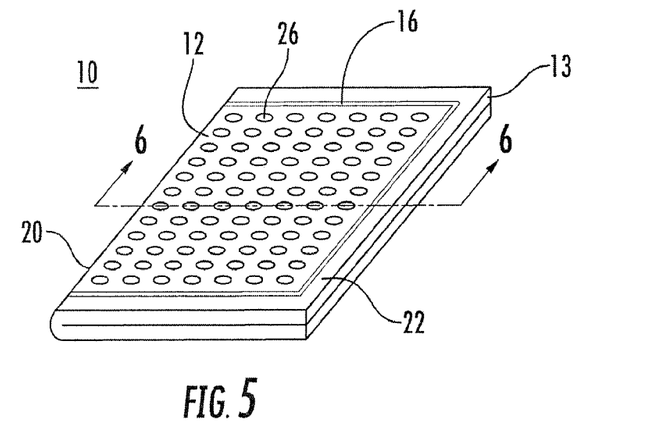
FIG. 5 is an front elevation view of an absorbent product with a liquid permeable pouch formed of one sheet of pouch material folded in half and sealed along the perimeter edges to form an enclosed space.
Figure 6:
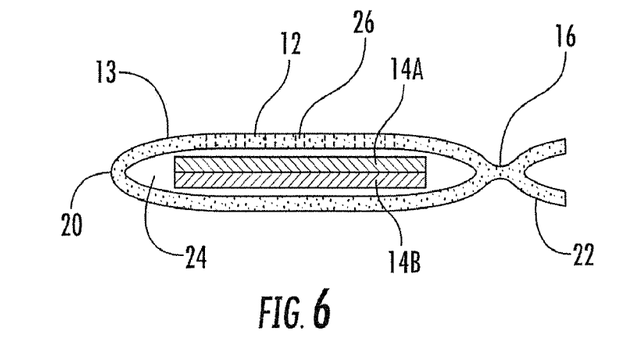
FIG. 6 is a cross-sectional view of the absorbent product of FIG. 5 showing two layers of absorbent material within the enclosed space formed by the liquid permeable pouch.
Figure 14:
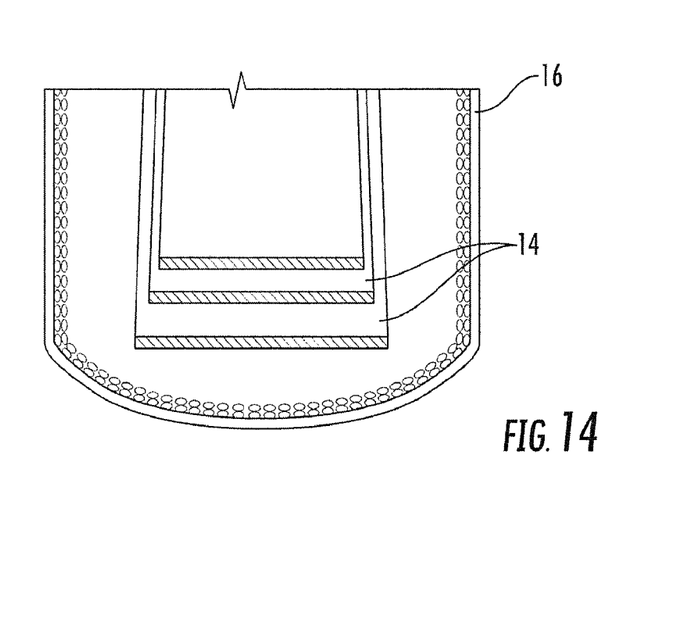
FIG. 14 is a cut away of the absorbent product of FIG. 13, where the upper sheet of pouch material has been removed exposing the absorbent material.

In some embodiments, the absorbent 14 is a sheet that is rolled, as shown in FIG. 3, while the sheet can be folded in other embodiments, such as the one shown in FIG. 4. As shown in FIGS. 6 & 14, in some embodiments, the absorbent 14 can be a sheet comprising a plurality of stabilized sheets of cellulosic material. In some embodiments, the absorbent 14 is a three dimensional foam material.

Figure 7:
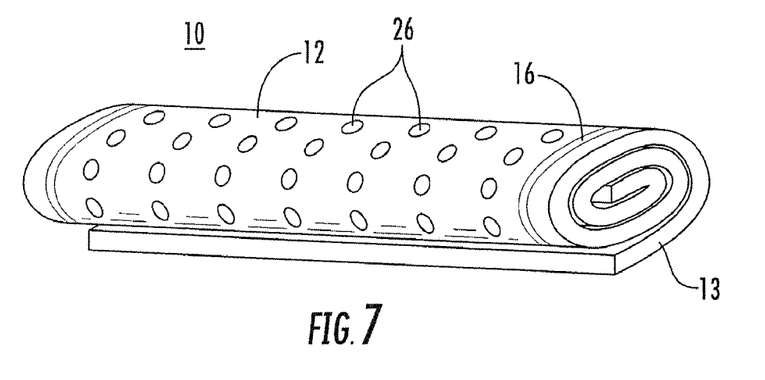
FIG. 7 is a front, perspective view of a rolled absorbent product.
Figure 8:
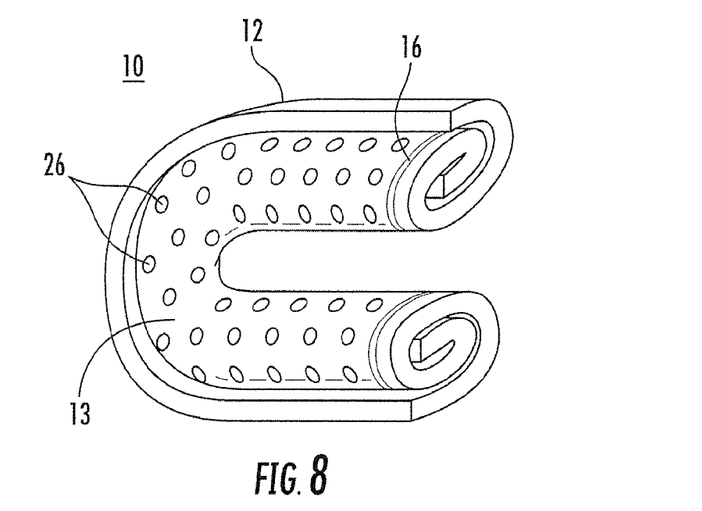
FIG. 8 is a front, perspective view of a rolled and folded absorbent product.

In some embodiments, such as the one in FIG. 7, the absorbent product 10 maintains a rolled configuration. In some embodiment, such as the one shown in FIG. 8, the absorbent product 10 can maintain a rolled and folded configuration. Such configurations can be maintained by thermal bonding, a string, a sleeve, such as a sleeve made of shrink-wrap materials, or a combination of these approaches.

Figure 9:
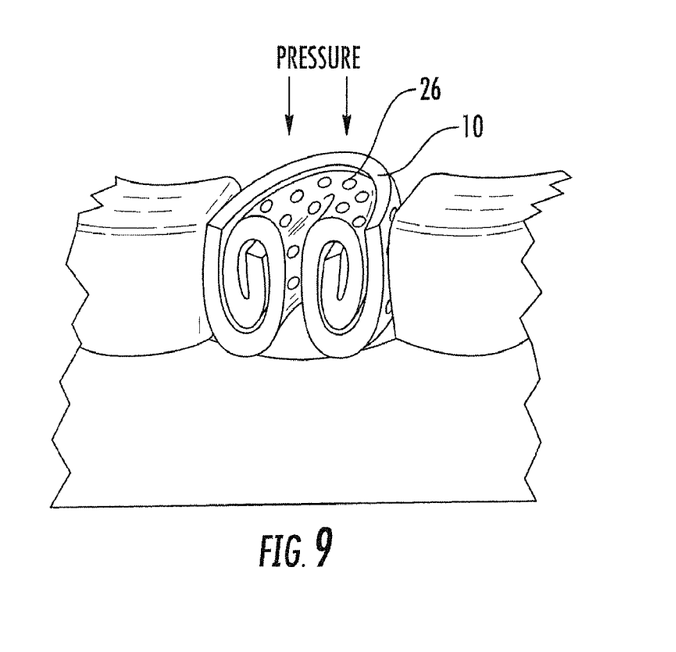
FIG. 9 is an environmental view showing a folded absorbent product with a rolled absorbent material, where the absorbent product has been placed between two teeth in a space where a tooth has fallen out or been removed.
Figure 10:
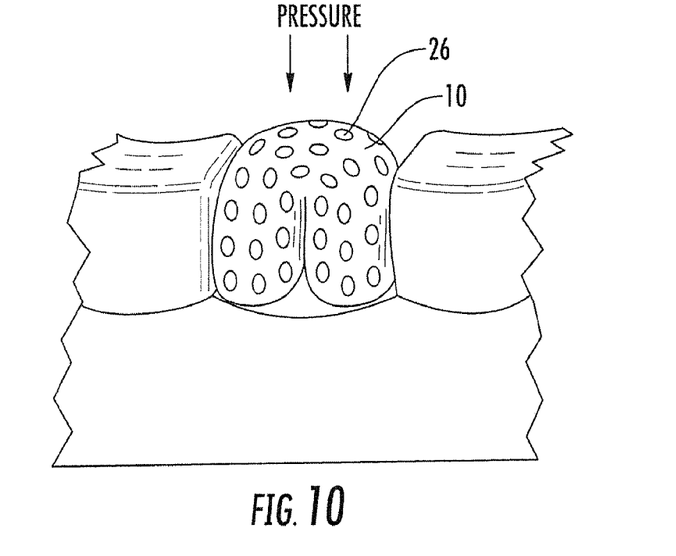
FIG. 10 is another environmental view showing a folded absorbent product with a rolled absorbent material, where the absorbent product has been placed between two teeth in a space where a tooth has fallen out or been removed.
Figure 11A:
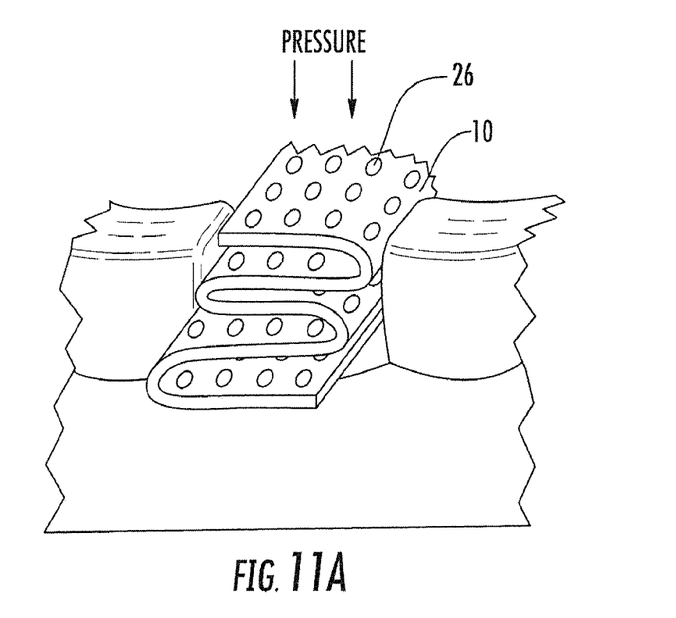
Figure 11B:
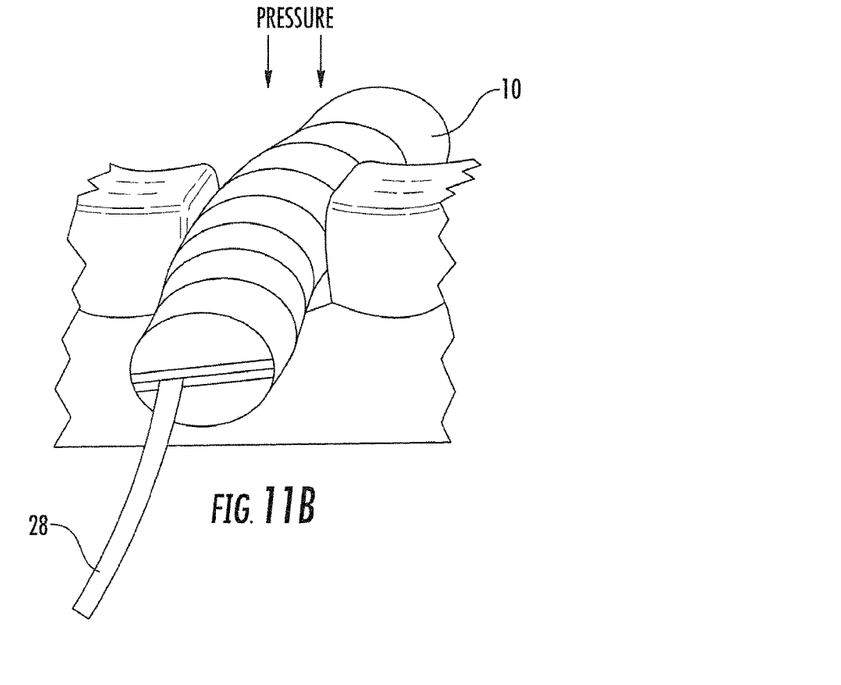
FIG. 11B is an environmental view showing an absorbent product with a folded or multi-layered absorbent material, wherein the absorbent product has been placed between two teeth in a space where a tooth has fallen out or been removed.

In some embodiments, the instructions 4 include rolling and/or folding the absorbent product, and placing the absorbent product proximate the site of the bleeding. In some embodiments, the instructions 4 can include placing the rolled and/or folded absorbent product against the site of the bleeding. In some embodiments, the instructions 4 can include placing the absorbent product 10 in a sulcus where there is bleeding, while the instructions 4 can include placing a rolled and/or folded absorbent product 10 in a sulcus where there is bleeding in other embodiments. FIGS. 9-11 show examples of an absorbent product 10 placed over a sulcus where a tooth has fallen out or was removed. In some instances, the absorbent material 14 can be rolled and/or folded, while the entire absorbent product 10 can be rolled and/or folded in other instances. In some embodiments, as shown in FIGS. 9-10, the absorbent material 14, but not the absorbent product 10, can be rolled and then entire absorbent product can be folded. In instances where a string 28 is bonded to the absorbent product 10, the instructions 4 can include placing the absorbent product 10 in a manner that the string extends from the mouth for easy retrieval of the absorbent product 10.

Figure 12A:
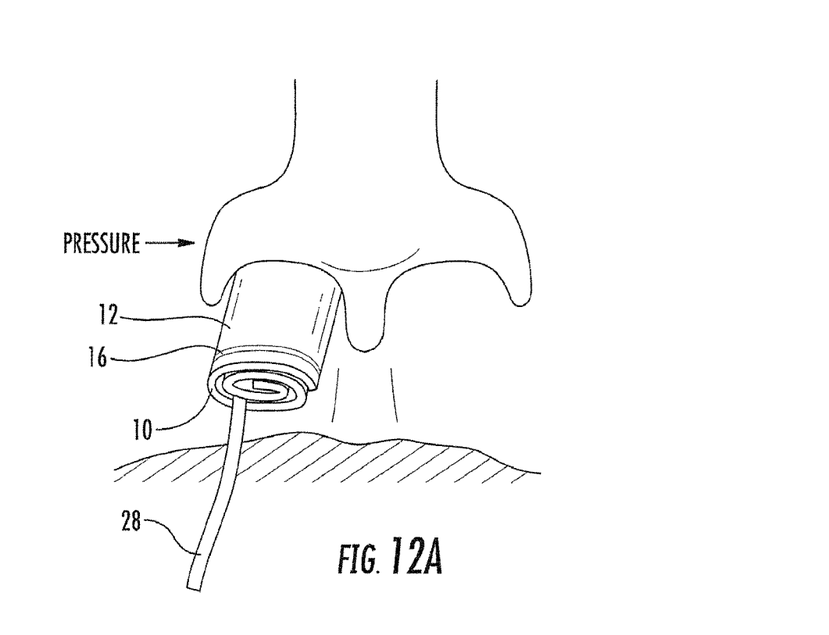
Figure 12B:
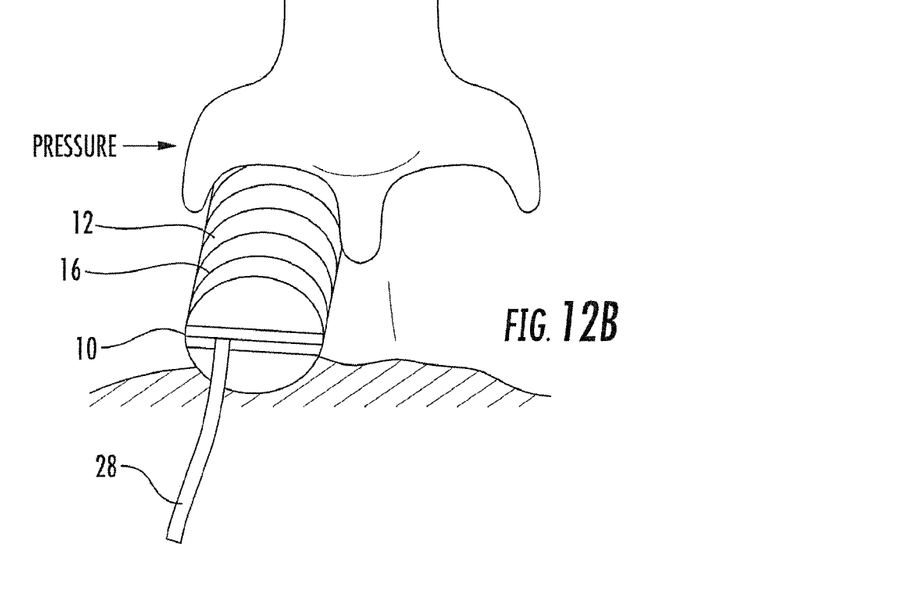
FIG. 12B is an environmental view showing an absorbent product with a rolled absorbent placed into a nostril to facilitate hemostasis of a bloody nose.

In other embodiments, the instructions 4 can include tilting the head backward to facilitate hemostasis. The instructions 4 can also include placing a portion of the absorbent product 10 in a nostril of an individual experiencing epistaxis (i.e., a nose bleed). In some embodiments, the instructions 4 can include rolling or folding the absorbent product 10 and inserting the rolled or folded absorbent product 10 into the nostril of the patient, as shown in FIG. 12A. In other embodiments, the instructions 4 can be adapted for an absorbent product 10 that includes an absorbent material 14 that is rolled and/or layered within the liquid permeable pouch 12 and inserting an end of the absorbent product 10 into the nostril of a person experiencing epistaxis, as shown in FIG. 12B. As shown in FIGS. 12A & 12B, the instructions 4 can include applying pressure to the nostril that is the site of the epistaxis. In instances where a string 28 is bonded to the absorbent product 10, the instructions 4 can include inserting the absorbent product 10 in a manner that the string 28 extends from the nostril for easy retrieval of the absorbent product 10. Even in embodiments where a string 28 is not present, the fact the liquid permeable pouch 12 is made from stable materials and extends beyond the absorbent material, facilitates easy removal of the absorbent product 10 even after being saturated with blood, mucous, or other bodily fluids.

In some embodiments, the absorbent product 10 can be designed so that the rolled or folded absorbent material 14 has a minor cross-sectional area that approximates the size of an adult nostril or tooth socket, or the nostril or tooth socket size of a child or teen. In other embodiments, the absorbent product can be sized so that, when rolled or folded, it assumes a minor cross-sectional area that approximates the size of an adult nostril or tooth socket, or the nostril or tooth socket size of a child or teen. Alternately, in either embodiment, the minor cross-sectional area can approximate half the size of an adult/child/teen nostril or tooth socket, so that the absorbent product fits snuggly in the nostril or tooth socket when folded in half.

In some embodiments, the instructions 4 can include applying pressure to an absorbent product 10 that has been placed on or proximate the source of the bleeding. The pressure is represented by arrows in FIGS. 9-11, and can be applied by a finger or by biting down with the opposing set of teeth (i.e., top teeth if the bottom tooth is out or the bottom teeth if an upper tooth is missing).

In some embodiments, the bleeding can originate from the nasal cavity (i.e., epistaxis). In such embodiments, the rolled absorbent product 10 can be inserted lengthwise into the nasal cavity, as shown in FIG. 12. In some embodiments, pressure can be applied by placing a finger against the side of the nose that is bleeding. In some embodiments, the pressure can be applied by squeezing the nose with one finger (e.g., pointer finger or long finger) and the thumb.

Figure 13:
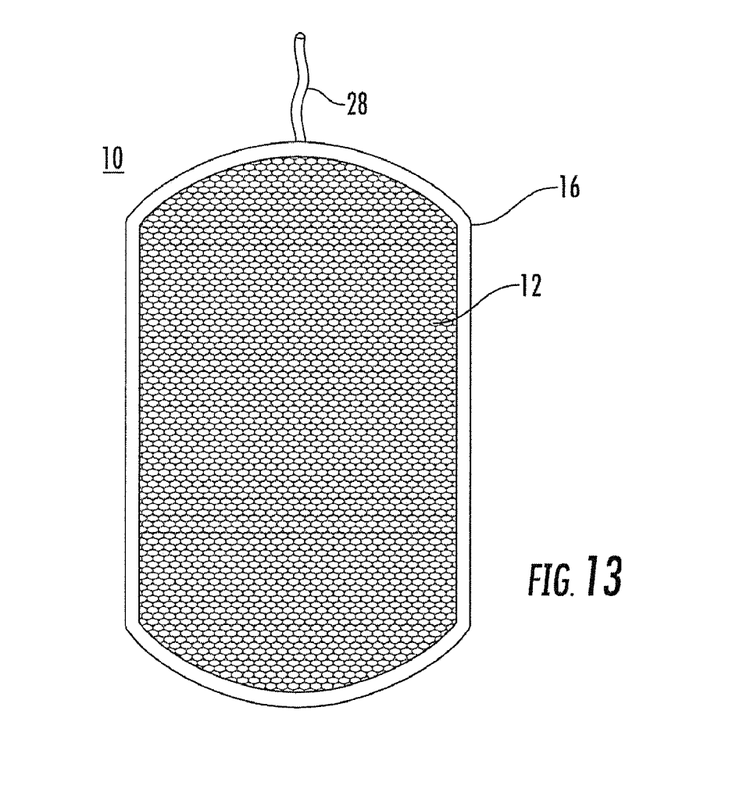
FIG. 13 is a top view of an absorbent product that includes a string.

In some embodiments, as shown in FIG. 13, the absorbent product 10 includes a string 28 extending from the liquid permeable pouch 12. The string 28 can be adapted for retrieving the liquid permeable pouch 12 from the mucosal membrane (e.g., the mouth, the nose, or the vaginal canal).

In some embodiments, the absorbent material 14 can include a coagulating material. Examples of coagulating materials include, but are not limited to, tannic acid, regenerated oxidized cellulose, gelatin sponges, collagen with or without fibrinogen, aluminum chloride, ferric chloride, chlorhexadine, and derivatives thereof. The coagulating material can be in a dried form, such as a powder or a coating. If a coating is used, it can be applied using techniques know in the art, such as, application as a solution containing the coagulating material and then drying the coagulating material on the absorbent substrate.

In some embodiments, the absorbent and/or the liquid permeable pouch can include a modified, soluble cellulose that thickens blood as it dissolves. Examples of modified, soluble cellulose materials include regenerated oxidize cellulose, such as that sold in woven form under the mark SURGICEL® by Ethicone.

Figure 15:
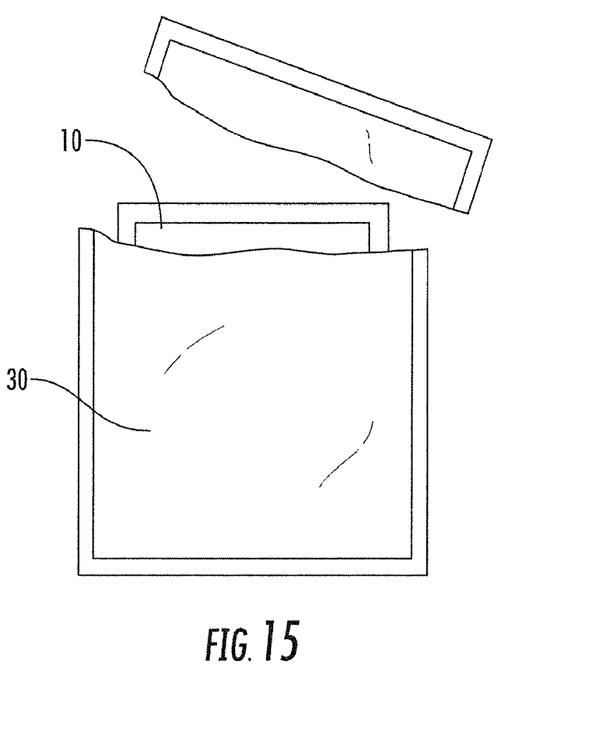
FIG. 15 is a front, perspective view showing a sterile pouch that has been torn along the upper edge to expose the absorbent product contained therein.
Figure 16:
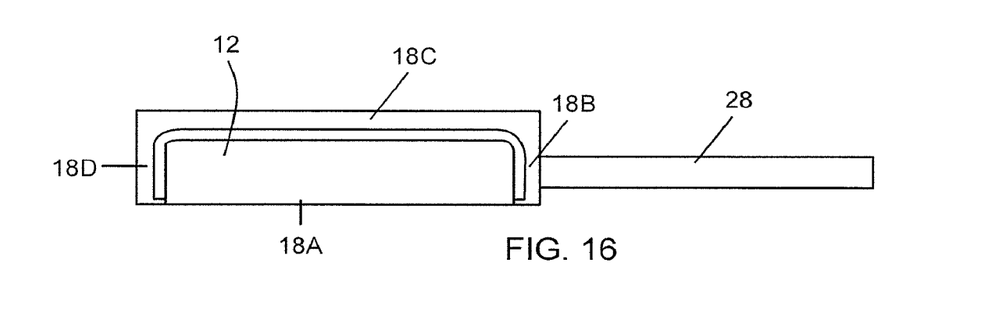
FIG. 16 is a top view of an elongated absorbent product including a string extending from one end thereof.

In some embodiments, the absorbent product 10 is contained within a sterile pouch 30, and the instructions 4 include removing the absorbent product 10 from the sterile pouch 30 before applying the absorbent product 10 to the bleeding tissue. An example of such an embodiment is shown in FIG. 15, where the sterile pouch 30 has been torn to show the absorbent product 10 contained within the sterile pouch 30. Using this approach, the absorbent product 10 can be sterilized during packaging and remain sterile until the absorbent product 10 is ready to be used.

In some more specific embodiments, the kit 2 can include an absorbent product 10 adapted for mucosal membrane hemostasis and instructions 4 for using the absorbent product 10. The kit 2 can be a first aid kit and can include additional products for providing aid. Examples include alcohol, elastic wraps, gauze, adhesive bandages, cotton swabs, etc.

The absorbent product 10 can include a liquid permeable pouch 12, and at least one piece (i.e., sheet or 3-D solid) of absorbent material 14 contained within the liquid permeable pouch 12. The instructions 4 can include rolling and/or folding the absorbent product 10, placing the rolled and/or folded absorbent product 10 proximate the site of the bleeding, and applying pressure to the absorbent product 10. Examples of rolled and/or folded absorbent products 10 placed proximate the site of bleeding are shown in FIGS. 9-12. Because the absorbent products 10 include a liquid permeable pouch 12 to stabilize and contain the absorbent material 14, the absorbent product can remain in a nostril, a tooth socket, or the vaginal canalfor an extended period of time (e.g., 30 minutes, 1 hour, 2 hours, etc.).

The absorbent products 10 can come in a variety of sizes. For example, some absorbent products 10 can be adapted for use by children or infants, while some absorbent products 10 can be adapted for use by adults. For example, absorbent products 10 adapted for children may be smaller in area, and may also include smaller amounts of absorbent material 14. In some embodiments, the diameter of the rolled absorbent material 14 or thickness of the folded or multiply absorbent material 14 can range from 1-4 cm (or 1-3 cm) in absorbent products adapted for use by adults and can range from 0.5-2.0 cm (or 0.5-1.5 cm) in absorbent products adapted for use by children. In some embodiments, the length (L) of the absorbent products 10 adapted for children can range from 2-4 cm, while the length (L) of absorbent products 10 adapted for adults can range from 3-6 cm. In some embodiments, the width of the absorbent products 10 adapted for children can range from 0.5-2.0 cm (or 0.5 to 1.5 cm), while the width of absorbent products 10 adapted for adults can range from 1-4 cm (or 1-3 cm).

In some embodiments, the kit 2 can include one or more absorbent products 10 adapted for use by children and one or more absorbent products 10 adapted for use by adults. In some embodiments, the absorbent products 10 adapted for use by children include a string 28. In some embodiments, the kit 2 can include other first aid products, such as adhesive absorbent products, antiseptic solutions (isopropyl alcohol, hydrogen peroxide, etc.), tape, scissors, gauze, etc.

In some embodiments, such as the ones shown in FIGS. 9 & 11, the instructions 4 include placing a width of the rolled and/or folded absorbent product 10 over the site of the bleeding. In some embodiments, such as the ones shown in FIGS. 10 & 12, the instructions include placing an end of the rolled and/or folded absorbent product 10 over the site of the bleeding.

In some embodiments, the absorbent product 10 can be flexible and/or compressible. For instance, in some embodiments, the absorbent product 10 can be folded in half even after it has been rolled. The flexibility facilitates comfort during use, as well as, the ability of the absorbent product 10 to conform to non-uniform shapes, such as the nostril or the sulcus from a missing tooth. The compressibility facilitates comfort when pressure is applied to an absorbent product 10 contacting the site of the bleeding, which may be tender.

A method of hemostasis in a mucosal membrane is also disclosed. The method can include providing any absorbent product 10 as disclosed herein, placing the absorbent product 10 proximate the site of the bleeding; and applying pressure to the absorbent product 10. The method can also include folding and/or rolling the absorbent product 10 before placing it proximate the site of the bleeding.

Dental practitioners, periodontists, oral surgeons, and physicians treat the mucus membranes of patients using surgical procedures on a daily basis. Bleeding as a result of these procedures is inevitable and clot formation in the "wet" environment of the mouth or nose becomes a significant challenge. Typically sutures, epinephrine, or cautery can be used intraorally or intranasal during surgical procedures to initiate hemostasis. In challenging locations, gelatin sponges or collagen products can be condensed (or "packed") into a wound by the surgeon to further assist in the development of hemostasis.

With the surge in ageing baby boomers, blood thinner medications to treat cardiac conditions have increased significantly. These medications include, but are not limited to aspirin, Coumadin®, Plavix®, and Effient®. Older medications like Aspirin and Coumadin® can be titrated and quantified which makes it easier to predict the susceptibility of a patient to have clotting complications following a surgical procedure. New age blood thinners like Plavix® and Effient® can have a "variable response" in patients, meaning that it is more effective in some people than in others. This can range from severe life threatening internal bleeding to no effect on bleeding at all. From a surgical perspective, there is no way to quantify how these medications are affecting the individual patient to be treated and the bleeding response the patient will have during and after a procedure. In addition, alcohol consumption can significantly reduce the body's ability to clot. This effect varies significantly based on the amount, length of time and habits of the individual patient. Several common chemotherapy medications, such as Avastin®, also predispose a patient to profuse bleeding from the mouth and gums.

Achieving clot formation after a surgical procedure in the intraoral or nasal environment is a challenge due to the constant dilution of the clotting cascade by saliva or nasal mucosal discharge. These difficulties can be increased tenfold by factors such as a patient's medical history, use of blood thinners, and alcohol consumption. Post-operative bleeding is a consequence commonly found with intra-oral and intranasal procedures and the typical patient instruction is to treat the wound by applying pressure or packing with regular gauze or biting on a tea bag. These methods do not always achieve hemostasis. Such considerations may also be applicable to menstruation or for surgical procedures involving the vaginal canal requiring post-operative hemostatic absorbents.

In some embodiments, the absorbent product can include a three dimensional absorbent (e.g., a cylinder, log-shaped, an elongated, rectangular solid, or spherical) contained within a liquid permeable pouch formed using heat sealed (thermally bonded) sheets of nylon mesh. In some embodiments, the absorbent can be formed from filter paper, or a similar absorbent, placed in layers. In some embodiments, the absorbent can be one or more three-dimensional solids. In some embodiments, the components of the absorbent product are nontoxic, porous, malleable, hydrophilic and can be irradiated prior to use. If required to achieve hemostasis with intraoral bleeding, in some embodiments, the user places the absorbent product over the wound and applies pressure either digital or through a masticatory (i.e., by biting on the absorbent product) hold. If required to achieve hemostasis with intranasal bleeding, in some embodiments, the user inserts the absorbent product within the nasal cavity and applies digital pressure to the outside skin of the nose.

In some embodiments, a string is attached to the absorbent product. Inclusion of a string can be particularly useful to prevent swallowing and allow for easy retrieval when placed within the mouth by a caregiver (e.g., when used with infants, children, medicated individuals, or other individuals who may not be able to retrieve the absorbent product themselves). The string can be used to facilitate easy retrieval of the absorbent product from the nostril or the vaginal canal as well.

In some embodiments, the absorbent product is sealed in an easily opened "tear away" foil packaging that eliminated contamination and air sensitivity of the product. The absorbent product could come in multiple sizes. In some embodiments, an absorbent product for adults would be roughly double the size of the absorbent product for infants and children. These absorbent products could be distributed for both professional and consumer use to assist in hemostasis of bleeding in the mouth or other mucosal membranes (e.g., epistaxis).

The absorbent product could be purchased by caregivers or by medical professionals for distribution to patients, particularly those at higher risk for post-operative bleeding. The absorbent products and kits can also be sold in pharmacies, grocery stores, and in big-box store environments. This can range from wound oozing after intraoral surgery to tooth eruption and exfoliation often associated with bleeding in children. The absorbent products described herein can be used by caregivers and consumers to assist in clot formation and hemostasis in a liquid environment like the mouth, nose, or vaginal canal.

Figure 17:
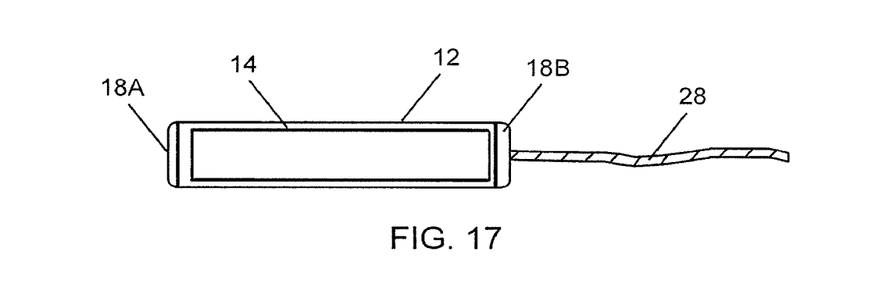
FIG. 17 is a semi-transparent view of another elongated absorbent product including a string extending from one end thereof.
Figure 18:
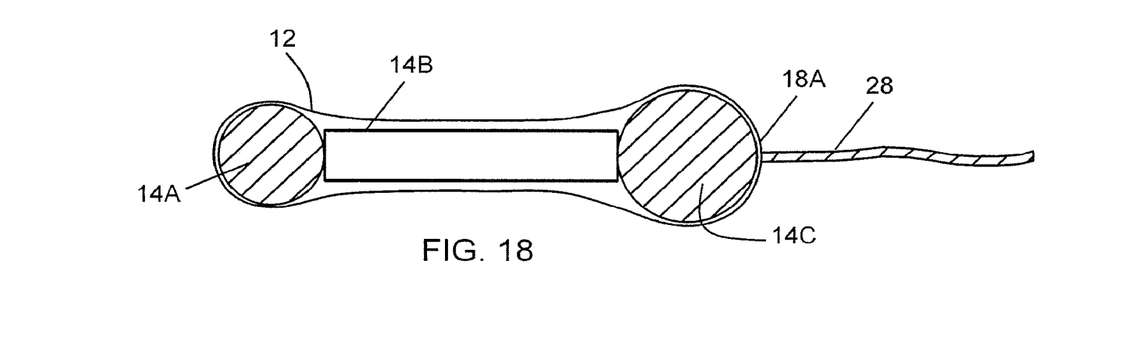
FIG. 18 is a semi-transparent view of another elongated absorbent product including a three piece absorbent and a string extending from one end thereof.

In some embodiments, as shown in FIGS. 17 and 18, the absorbent product 10 can be a tampon for insertion into the vaginal canal. In some embodiments, the absorbent product 10 can include a three-dimensional absorbent. In some embodiments, the absorbent product 10 is sold with instructions 4 for use of the absorbent product as a tampon. For example, the instructions 4 can include gentle insertion of the absorbent product 10 through the introital opening and into the vaginal canal either with or without an applicator. The instructions 4 can include suggested frequency for changing the tampon, such as every 4 hours, every 6 hours, or every 8 hours. The instructions 4 can include removal of the absorbent product 10 using the string 28 after a wear time of 4 hours, 6 hours, or 8 hours.

FIG. 17 shows a semi-transparent view of an absorbent product 10 that includes a liquid permeable pouch 12 formed from a sleeve that is bonded at each end 18A, 18B with a string 28 extending from one end of the liquid permeable pouch 12. The absorbent 14 within the liquid permeable pouch can be a three-dimensional absorbent, such as a cylindrical foam element, a cylindrical cotton element, a paper roll (e.g., a hollow tube of rolled filter paper), or a combination thereof (e.g., a paper roll filled with cotton or foam). The absorbent 14 can be selected so that it is sufficiently rigid to facilitate easy insertion of the absorbent product 10 into the vaginal cavity without a secondary applicator. In other embodiments, the absorbent 14 can be more flexible and require an applicator to facilitate insertion of the absorbent product 10 into the vaginal cavity.

FIG. 18 shows a semi-transparent view of another absorbent product that includes a liquid permeable pouch 12 formed from a sleeve that is bonded at one end 18A with a string 28 extending from the bonded end. In FIG. 18, the absorber 14 includes three portions: a protective, cushioning bulb 14A, a cylindrical portion 14B, and a retention bulb 14C proximate the string 28. In some embodiments, the cushioning bulb 14A and the retention bulb 14C can be formed of a resilient absorbent material, such as an open cell foam (e.g., PVA foam) or cotton, while the intermediate absorbent 14B can be formed from a cylindrical foam, a paper roll (e.g., a hollow tube formed of rolled filter paper), or a combination thereof (e.g., a paper roll filed with cotton or foam). The intermediate absorbent 14B can be selected so that it is sufficiently rigid to facilitate easy insertion of the absorbent product 10 into the vaginal cavity without a secondary applicator. In other embodiments, the absorbent 14 can be more flexible and require an applicator to facilitate insertion of the absorbent product 10 into the vaginal cavity. The cushioning bulb 14A material can be selected for comfortable and gentle insertion of the absorbent product 10 through the introital opening and into the vaginal canal. Finally, the retention bulb 14C can be selected of a resilient material that helps maintain the absorbent product 10 within the vaginal canal and prevent leakage of menstrual fluid.

In some embodiments, the retention bulb 14C can have a dimension large than the cushioning bulb 14A, and both the retention bulb 14C and the cushioning bulb 14A can have a dimension that is larger than the intermediate absorbent 14B. For example, in some embodiments a radius of the intermediate absorbent 14B can be 0.3 to 0.7 inches, while the radius of the cushioning bulb 14A can be 0.6 to 0.9 inches and the radius of the retention bulb 14C can be 0.7 to 1.2 inches. In some embodiments, a ratio of the radius of the cushioning bulb to the radius of the retention bulb can range from 1:1.2 to 1:2.

General Examples

As evident from the description above, the absorbent products can be sized for use by children, teens, and/or adults. The absorbent products can be used in a wide variety of environments and settings. For instance, the absorbent products can be used by consumers, care-givers, and medical professionals.

In some instances, the absorbent product can include an absorbent material that is folded or rolled or can be folded or rolled to approximate the width of an average child's tooth socket and/or nasal orifice. The absorbent product could then be used by a child experiencing normal baby-tooth exfoliation, which typically incurs bleeding on loosening, tooth loss, and eruption of the adult tooth. The soft components of the absorbent product would then allow for easy use in a tender area of a child's mouth. The capillary action isolates the blood in the absorbent material where it is obscured from the user by the liquid permeable pouch. This design decreases the potential for fear and emotion by a child (or parent) when bleeding of the mouth is observed. Such devices would be useful after dental or nasal trauma is experienced by a child.

In other embodiments, the absorbent product can be sized to approximate the width of an average adult tooth socket and/or nasal orifice when folded or rolled (any may be folded or rolled within the liquid permeable pouch). The absorbent product could be used by any adult experiencing hemorrhaging associated with dental bleeding common after oral surgical and periodontal procedures. Alternately, the absorbent product could be utilized to control nose bleeds that are a common side effect of blood thinner medications or nasal procedures, such as rhinoplasty or sinus surgery. The absorbent product could also be used in connection with any other dental or nasal trauma experienced by a teen or an adult.

In other embodiments, the absorbent products could be utilized by dentists, pediatric dentists, periodontists, and oral surgeons as a post-operative adjunct to treat hemorrhage typical with any intraoral procedure. The absorbent products could also be utilized by physicians performing surgery in the nasal cavity to utilize as a post-operative adjunct for treatment of hemorrhage typical with nasal procedures, such as a rhinoplasty or sinus surgery. The absorbent products could also be distributed by surgeons to patients who are recovering from a medical procedure.

The absorbent products described herein may exhibit reduced leakage compared to tampons currently available on the market. In particular, it is believed that when the liquid permeable pouch is formed from a mesh sleeve, the mesh sleeve is resilient and will exert pressure on the absorbent during use. In contrast, many current tampon products include an outer wrap formed from a spun bond material which can separate from the absorbent once exposed to fluid and/or moisture. It is believed that the absorbent products described herein will improve absorption during use and prevent leakage.

Specific Examples

In order to evaluate the efficacy of the absorbent products described herein over a similar application using gauze, prototypes were produced using nylon mesh as the liquid permeable pouch and filter paper as the absorbent material. The combination of the hydrophilic liquid permeable pouch material and filter paper absorbent was far superior to gauze in terms of absorbency and fluid distribution. It is believed that the absorbent products described herein are superior to gauze because the hydrophilic liquid permeable pouch allowed blood to freely pass through to the absorbent, but prevented mucous from being absorbed by the filter paper.

The examples were produced using nylon mesh with 36% open area, mesh openings of 78 µm, a mesh count of 77 per cm, a thread diameter of 48 µm, a basis weight of 43 gsm, and a thickness of 80 µm (Saatifil® PES 78/36 sold by Saati S.p.a.) and a filter paper with a high intake rate (440 mls/m in) and retention (30 microns), such as Grade 963 available from Ahlstrom Filtration LLC. An experienced Board Certified Periodontist applied the example prototype absorbent product to a blood source. Compared with a rolled gauze, the example absorbent product exhibited significantly improved absorption, fluid retention within the liquid permeable pouch, and fluid distribution. In addition, the example absorbent product was much easier to place for both the surgical practitioner and the patient than traditional gauze. Upon inspection of the used example absorbent products, mucosal fluids were consistently excluded by the outside nylon mesh from the inside absorbent filter paper, while blood passed through the nylon mesh and into the absorbent filter paper. Capillary action of blood within the inner absorbent material kept the blood within the absorbent product and prevented release of the slurry of blood and blood components commonly observed with traditional gauze.

In another study, absorbent materials were placed within a Saati Care Hyphyl™ Nylon Mesh sleeve. In particular, the absorbents evaluated were gauze, filter paper, cotton, and PVA foam. Prototypes were prepared by placing each absorbent inside a mesh sleeves and then heat sealing each end of the mesh sleeve. Prototypes of each absorbent material were placed in a beaker containing 10 mL of porcine plasma and observations were made about absorption rate. Prototypes of each absorbent material were also placed in a beaker containing 10 mL of bovine blood and observations were made about absorption rate. From this study, it was determined that the PVA foam was the best absorbent, while the cotton absorbent outperformed the filter paper. The PVA foam, cotton, and filter paper all performed better than conventional gauze. It should be noted that the entire 10 mL of plasma/blood were absorbed in under 1 minute for both the PVA foam and the cotton.

It was also observed that PVA foam prototypes performed best when there was a space between the end of the foam and the seal on the mesh of at least 1 mm (or at least 2 mm), to allow the foam to expand upon contact with liquid. In contrast, it was observed that the cotton and filter paper had improved absorption when they were packed tightly into the nylon mesh (i.e., no gap between the absorbent and the seal at the ends).

The foregoing is provided for purposes of illustrating, explaining, and describing embodiments of this invention. Modifications and adaptations to these embodiments will be apparent to those skilled in the art and may be made without departing from the scope or spirit of this invention.

What is claimed is:

1. An absorbent tampon comprising:
   a liquid permeable pouch,
   a three-dimensional absorbent material contained within the liquid permeable pouch; and
   a string extending outward from a first end of the liquid permeable pouch,
   wherein the three-dimensional absorbent material comprises a retention bulb at the first end of the liquid permeable pouch, a cushioning bulb at a second end of the liquid permeable pouch opposite the first end, and a hollow tubular portion disposed between the cushioning bulb and the retention bulb,
   wherein the liquid permeable pouch is adapted to contact the hollow tubular portion during use;

wherein the cushioning bulb and the retention bulb are separate from one another and project longitudinally and radially outward from opposite ends of the hollow tubular portion, wherein the retention bulb is larger than the cushioning bulb, and wherein the cushioning bulb and the retention bulb are formed of an absorbent foam material.

2. The absorbent tampon of claim 1, wherein the hollow tubular portion comprises a hollow paper cylinder, and both the inner and outer surfaces are paper.

3. The absorbent tampon of claim 2, wherein the retention bulb, the cushioning bulb, and the hollow tubular portion are formed as discrete elements.

4. The absorbent tampon of claim 1, wherein each of the retention bulb and the cushioning bulb have a dimension that is larger than a diameter of the hollow tubular portion.

5. The absorbent tampon of claim 1, wherein a radius of the hollow tubular portion ranges from 0.3 to 0.7 inches.

6. The absorbent tampon of claim 1, wherein the three-dimensional absorbent material is adapted to be retained within a vagina of a user during use.

7. The absorbent tampon of claim 1, wherein the cushioning bulb is spherical.

8. The absorbent tampon of claim 1, wherein the liquid permeable pouch is adapted to contact the hollow tubular portion upon insertion into a vagina of a user.

9. The absorbent tampon of claim 1, wherein the hollow tubular portion is filled with the foam material.

10. The absorbent tampon of claim 1, wherein the hollow tubular portion is filled with the foam material.

11. An absorbent tampon comprising:
a liquid permeable pouch, and
a three-dimensional absorbent material contained within the liquid permeable pouch; and
a string extending outward from a first end of the liquid permeable pouch,
wherein the three-dimensional absorbent material comprises a retention bulb at the first end of the liquid permeable pouch, a cushioning bulb at a second end of the liquid permeable pouch opposite the first end, and a hollow tubular portion disposed between the cushioning bulb and the retention bulb,
wherein the cushioning bulb and the retention bulb are separate from one another and project longitudinally and radially outward from opposite ends of the hollow tubular portion,
wherein the liquid permeable pouch is adapted to contact the hollow tubular portion during use;
wherein the hollow tubular portion comprises a hollow paper cylinder, and both the inner and outer surfaces are paper, and
wherein the cushioning bulb and the retention bulb are formed of an absorbent foam material.

12. The absorbent tampon of claim 11, wherein a radius of the hollow tubular portion ranges from 0.3 to 0.7 inches.

13. The absorbent tampon of claim 11, wherein the three-dimensional absorbent material is adapted to be retained within a vagina of a user during use.

14. The absorbent tampon of claim 11, wherein the cushioning bulb is spherical.

15. The absorbent tampon of claim 11, wherein the liquid permeable pouch is adapted to contact the hollow tubular portion upon insertion into a vagina of a user.

* * * * *